US011077085B2

(12) United States Patent
Dabdoub

(10) Patent No.: US 11,077,085 B2
(45) Date of Patent: Aug. 3, 2021

(54) DIETARY MACRO/MICRONUTRITIONAL SUPPLEMENT FOR PATIENTS UNDERGOING KIDNEY DIALYSIS

(71) Applicant: Atif Dabdoub, Atlanta, GA (US)

(72) Inventor: Atif Dabdoub, Atlanta, GA (US)

(73) Assignee: Atif Dabdoub, Atlanta, GA (US)

( * ) Notice: Subject to any disclaimer, the term of this patent is extended or adjusted under 35 U.S.C. 154(b) by 0 days.

(21) Appl. No.: 16/326,250

(22) PCT Filed: Aug. 23, 2017

(86) PCT No.: PCT/US2017/048126
§ 371 (c)(1),
(2) Date: Feb. 18, 2019

(87) PCT Pub. No.: WO2018/039297
PCT Pub. Date: Mar. 1, 2018

(65) Prior Publication Data
US 2019/0209507 A1  Jul. 11, 2019

Related U.S. Application Data

(60) Provisional application No. 62/379,872, filed on Aug. 26, 2016.

(30) Foreign Application Priority Data

Sep. 23, 2016  (SE) .................................. 1651259-2

(51) Int. Cl.
| | |
|---|---|
| *A61K 31/205* | (2006.01) |
| *A23L 33/16* | (2016.01) |
| *A23L 33/125* | (2016.01) |
| *A61K 47/02* | (2006.01) |
| *A23L 33/15* | (2016.01) |
| *A61K 36/736* | (2006.01) |
| *A61K 33/30* | (2006.01) |
| *A61K 36/45* | (2006.01) |
| *A61K 33/26* | (2006.01) |
| *A61K 9/00* | (2006.01) |
| *A23L 33/105* | (2016.01) |
| *A23L 33/155* | (2016.01) |
| *A61P 13/12* | (2006.01) |
| *A61K 9/14* | (2006.01) |
| *A61K 31/202* | (2006.01) |
| *A61K 31/295* | (2006.01) |
| *A61K 31/375* | (2006.01) |
| *A61K 31/4188* | (2006.01) |
| *A61K 31/4415* | (2006.01) |
| *A61K 31/455* | (2006.01) |
| *A61K 31/51* | (2006.01) |

(Continued)

(52) U.S. Cl.
CPC .............. *A61K 31/205* (2013.01); *A23L 2/52* (2013.01); *A23L 33/105* (2016.08); *A23L 33/125* (2016.08); *A23L 33/15* (2016.08); *A23L 33/155* (2016.08); *A23L 33/16* (2016.08); *A23L 33/175* (2016.08); *A61K 9/0053* (2013.01); *A61K 9/14* (2013.01); *A61K 31/122* (2013.01); *A61K 31/191* (2013.01); *A61K 31/194* (2013.01); *A61K 31/201* (2013.01); *A61K 31/202* (2013.01); *A61K 31/295* (2013.01); *A61K 31/352* (2013.01); *A61K 31/375* (2013.01); *A61K 31/4188* (2013.01); *A61K 31/4415* (2013.01); *A61K 31/455* (2013.01); *A61K 31/51* (2013.01); *A61K 31/519* (2013.01); *A61K 31/525* (2013.01); *A61K 31/593* (2013.01); *A61K 31/714* (2013.01); *A61K 33/04* (2013.01); *A61K 33/26* (2013.01); *A61K 33/30* (2013.01); *A61K 36/45* (2013.01); *A61K 36/736* (2013.01); *A61K 36/752* (2013.01); *A61K 36/9066* (2013.01); *A61K 47/02* (2013.01); *A61K 47/36* (2013.01); *A61P 13/12* (2018.01); *A23V 2002/00* (2013.01)

(58) Field of Classification Search
None
See application file for complete search history.

(56) References Cited

U.S. PATENT DOCUMENTS

| | | |
|---|---|---|
| 4,992,282 A | 2/1991 | Mehansho et al. |
| 5,714,168 A | 2/1998 | Stroh et al. |

(Continued)

FOREIGN PATENT DOCUMENTS

| | | | |
|---|---|---|---|
| JP | 2000264844 A | * | 9/2000 |
| JP | 2007001922 A | * | 1/2007 |

(Continued)

OTHER PUBLICATIONS

Lakhanpal et al. Internet Journal of Medical Update 2007 2(2):22-37 (Year: 2007).*

(Continued)

*Primary Examiner* — Robert A Wax
*Assistant Examiner* — Caralynne E Helm
(74) *Attorney, Agent, or Firm* — Thomas|Horstemeyer, LLP

(57) ABSTRACT

Provided herein is a nutritional supplement designed to support kidney and cardiac function as well as mitochondrial energy function needs in patients undergoing hemodialysis. This supplement replenishes essential vitamins and minerals that are lost during dialysis, does not contain compounds that may specifically cause harm to dialysis patients, and provides support for tissues undergoing oxidative stress.

10 Claims, No Drawings

(51) Int. Cl.

| | |
|---|---|
| A61K 31/525 | (2006.01) |
| A61K 31/593 | (2006.01) |
| A61K 31/714 | (2006.01) |
| A61K 33/04 | (2006.01) |
| A61K 36/752 | (2006.01) |
| A61K 36/9066 | (2006.01) |
| A23L 33/175 | (2016.01) |
| A23L 2/52 | (2006.01) |
| A61K 31/122 | (2006.01) |
| A61K 31/191 | (2006.01) |
| A61K 31/194 | (2006.01) |
| A61K 31/201 | (2006.01) |
| A61K 31/352 | (2006.01) |
| A61K 31/519 | (2006.01) |
| A61K 47/36 | (2006.01) |

(56) References Cited

U.S. PATENT DOCUMENTS

| | | | | |
|---|---|---|---|---|
| 6,696,492 | B1* | 2/2004 | Cavazza | A61K 31/205 514/556 |
| 6,995,166 | B1* | 2/2006 | Giordano | A23L 33/15 424/439 |
| 8,183,227 | B1 | 5/2012 | Perrin et al. | |
| 8,501,248 | B1* | 8/2013 | Sugerman | A61K 31/675 424/725 |
| 8,617,617 | B2* | 12/2013 | Giordano | A61K 31/07 424/638 |
| 9,176,146 | B2* | 11/2015 | Theoharides | A61K 31/00 |
| 2002/0155163 | A1 | 10/2002 | Benjamin | |
| 2003/0157083 | A1* | 8/2003 | Udell | A61K 9/4858 424/94.1 |
| 2004/0082536 | A1 | 4/2004 | Cooper | |
| 2004/0137080 | A1* | 7/2004 | Cremisi | A61K 33/04 424/702 |
| 2005/0191386 | A1* | 9/2005 | Adams | A23L 2/52 426/72 |
| 2006/0083824 | A1* | 4/2006 | Manning | A23L 33/175 426/72 |
| 2006/0088574 | A1* | 4/2006 | Manning | A23L 33/12 424/439 |
| 2006/0292217 | A1* | 12/2006 | Schmidt | A61K 9/4825 424/456 |
| 2007/0036870 | A1* | 2/2007 | Bryan | A21D 2/02 424/642 |
| 2008/0187526 | A1 | 8/2008 | Prasad et al. | |
| 2008/0287368 | A1* | 11/2008 | Yu | A61K 31/015 514/7.7 |
| 2008/0317725 | A1* | 12/2008 | Baum | A61K 31/05 424/94.1 |
| 2009/0297492 | A1* | 12/2009 | Satoh | A61K 9/4858 424/94.1 |
| 2010/0010005 | A1* | 1/2010 | Lines | A61K 31/352 514/252.16 |
| 2010/0022629 | A1* | 1/2010 | Liu | A61K 31/385 514/440 |
| 2010/0047363 | A1 | 2/2010 | Wigneswaran | |
| 2010/0190739 | A1* | 7/2010 | Sutterer | A61K 31/07 514/52 |
| 2010/0260836 | A1 | 10/2010 | Giordano et al. | |
| 2011/0280851 | A1 | 11/2011 | Herzlinger et al. | |
| 2012/0269868 | A1 | 10/2012 | Faerstein | |
| 2013/0059768 | A1* | 3/2013 | Hallaraker | A61K 31/683 514/1.1 |
| 2014/0107201 | A1 | 4/2014 | Williams et al. | |
| 2014/0107223 | A1 | 4/2014 | Brown | |
| 2015/0118298 | A1* | 4/2015 | Zhang | A61K 31/122 424/456 |
| 2015/0209306 | A1* | 7/2015 | Bredesen | A61K 31/122 424/94.1 |
| 2016/0199337 | A1 | 7/2016 | Morris | |
| 2016/0199385 | A1 | 7/2016 | Sciavolino et al. | |
| 2016/0235822 | A1 | 8/2016 | Holstein et al. | |
| 2017/0128486 | A1* | 5/2017 | Desbarats | A61K 33/02 |

FOREIGN PATENT DOCUMENTS

| | | |
|---|---|---|
| WO | 1999007419 | 2/1999 |
| WO | 2002026221 | 4/2002 |
| WO | 2003032751 | 4/2003 |
| WO | 2005123108 | 12/2005 |
| WO | 2010077878 | 7/2010 |
| WO | 2013072767 | 5/2013 |
| WO | 2014155370 | 10/2014 |
| WO | 2015034984 | 3/2015 |
| WO | 2016053903 | 4/2016 |
| WO | 2018039297 | 3/2018 |

OTHER PUBLICATIONS

Milam greatist.com/health/ultimate-guide-vitamins-and-minerals#1 19 pages (Year: 2013).*
Volek www.nutritionexpress.com/showarticle.aspx?articleid=1487 6 pages (Year: 2011).*
Anderson et al. Journal of Chemical Education 2000 77(3) 359-360 (Year: 2000).*
Wikipedia: Hemodialysis <https://en.wikipedia.org/wiki/Hemodialysis> 12pp, accessed Apr. 23, 2019.
Wikipedia: Ubiquinol <https://en.wikipedia.org/wiki/Ubiquinol> 4pp, accessed Apr. 23, 2019.
International Search Report and Written Opinion for PCT/US19/19171, 16pp, dated May 13, 2019.
International Preliminary Report on Patentability for PCT/US2017/048126 dated Dec. 13, 2018, 13pp.
International Search Report and Written Opinion for PCT/US2017/048126 dated Oct. 25, 2017, 11 pp.
Maniglia et al., "The Role of Nutrition and Supplementation in Dialysis Patient Health," Glucose Intake and Utilization in Pre-Diabetes and Diabetes, 2015, Elsevier Science, Ronald Ross Watson and Betsy Dokken, editors, 7pp.
Swedish Office Action for 1651259-2 dated Oct. 3, 2017, 7pp.
Swedish Office Action for 1651259-2 dated Sep. 3, 2018, 5pp.
Swedish Search Report for 1651259-2 dated Oct. 3, 2017, 2pp.
European Search Report dated Mar. 4, 2020 for European Application 17844320.6 (8pp).
Cato et al., Evaluation for: Dialysis Supplement for Kidney Patients Undergoing Dialysis Treatment 2017-2019., RENUSU Recovery Supplements., Jan. 29, 2020., pp. 1-13.
Hu et al., Effects of Omega-3 Fatty Acids on Markers of Inflammation in Patients with Chronic Kidney Disease: A Controversial Issue., Ther Apher Dial., Apr. 2018., pp. 124-132., vol. 22-1., <https://www.ncbi.nlm.nih.gov/pmc/articles/PMC5880693/>.
Lauretani et al., Omega-3 and Renal Function in Older Adults., Curr Pharm Des., 2009., pp. 4149-4156., vol. 15-36., <https://www.ncbi.nlm.nih.gov/pmc/articles/PMC2863302/>.
Kasemy et al., Effect of Omega-3 supplements on quality of life among children on dialysis., Oct. 2, 2020., vol 99-40., <https://www.ncbi.nlm.nih.gov/pmc/articles/PMC7535790/>.

* cited by examiner

DIETARY MACRO/MICRONUTRITIONAL SUPPLEMENT FOR PATIENTS UNDERGOING KIDNEY DIALYSIS

CROSS REFERENCE TO RELATED APPLICATIONS

This application claims priority upon U.S. provisional application Ser. No. 62/379,872, filed Aug. 26, 2016 and Swedish application no. 1651259-2 filed on Sep. 23, 2016. These applications are hereby incorporated by reference in their entireties for all of their teachings.

BACKGROUND

The kidneys of an adult human filter approximately 190 liters of blood daily; due to their role, these organs are susceptible to damage and dysfunction that may progress, over time, to disease. Chronic Kidney Disease (www.life-extension.com) High blood pressure, elevated blood sugar (including the presence of diabetes), high-protein diets, smoking, obesity, family history of kidney disease or failure, and a patient's history of heart problems all threaten the health of the kidneys, inflicting damage that has the potential to be lethal. In many cases, when the kidneys fail to perform adequately, kidney dialysis is required.

Essential amino acids such as L-carnitine can be essentially lost (70-80%) during dialysis; L-carnitine deficiency is associated with muscle aches and fatigue, confusion, hypoglycemia, cardiomyopathy, fatty liver, muscle necrosis, abnormal lipid storage, and other conditions.

Oxidative stress, which is caused by an excess of free radicals and harmful molecules that can damage basic cellular constituents such as lipids, proteins, and DNA, can result from L-carnitine deficiency and is an especially dangerous condition for patients undergoing dialysis. Inadequate energy management in cardiac tissues brought on by L-carnitine deficiency can lead to cardiovascular complications including heart attack and heart failure. Further stressors include an excessive filtration burden on the kidneys resulting from the need to handle advanced glycation and lipoxidation end products and inflammation, especially when kidney function decreased to the point that dialysis is required.

Many essential nutrients, including water-soluble vitamins such as B complex vitamins and vitamin C and minerals such as zinc and selenium are depleted from the body during dialysis treatment. Further, other nutrients such as vitamin D, which is primarily produced by the healthy kidney and, in case of kidney failure, vitamin D synthesis ceases, or, is significantly affected. Other nutrients, however, such as fat-soluble vitamins, can accumulate in the tissues to dangerous levels in dialysis patients and should not be supplemented.

What is needed is a nutritional supplement that can replenish the supply of basic nutrients to the body that are lost by dialysis, without providing the excess of fat soluble vitamins that could be damaging in high quantities. Ideally, this supplement would also provide nutrients, including but not limited to L-carnitine, that support overall kidney health and combat the effects of oxidative stress. In addition to replenishing these essential nutrients, the supplement would ideally provide coenzyme Q10, which is a key component of the mitochondrial electron transport chain that is known to be important to mitochondrial energy generation (i.e., ATP synthesis). Finally, polyunsaturated fatty acids such as, for example, marine omega 3 fatty acids, are also removed from the body with chronic kidney dialysis. These compounds are lipid soluble macronutrients that are important to metabolism (i.e., energy production captured in the form of ATP).

The present invention addresses these needs by providing a nutritional supplement that will address the damaging effects of chronic kidney dialysis on the body.

SUMMARY

Provided herein is a nutritional supplement designed to support kidney and cardiac function as well as mitochondrial energy function needs in patients undergoing hemodialysis. This supplement replenishes essential vitamins and minerals that are lost during dialysis, does not contain compounds that may specifically cause harm to dialysis patients, and provides support for tissues undergoing oxidative stress.

The advantages of the materials, methods, and devices described herein will be set forth in part in the description that follows, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

DETAILED DESCRIPTION

Before the present materials, articles, and/or methods are disclosed and described, it is to be understood that the aspects described below are not limited to specific compounds, synthetic methods, or uses, as such may, of course, vary. It is also to be understood that the terminology used herein is for the purpose of describing particular aspects only and is not intended to be limiting.

In the specification and in the claims that follow, reference will be made to a number of terms that shall be defined to have the following meanings:

It must be noted that, as used in the specification and the appended claims, the singular forms "a," "an," and "the" include plural referents unless the context clearly dictates otherwise. Thus, for example, reference to "a citrus bioflavonoid" includes mixtures of two or more citrus bioflavonoids, and the like.

"Optional" or "optionally" means that the subsequently described event or circumstance can or cannot occur, and that the description includes instances where the event or circumstance occurs and instances where it does not. For example, the nutritional supplements described herein may optionally contain turmeric, where the turmeric may or may not be present.

As used herein, the term "about" is used to provide flexibility to a numerical range endpoint by providing that a given value may be "a little above" or "a little below" the endpoint without affecting the desired result.

"Unit dose" refers to a discrete amount of formulation to be administered to a subject. The compositions and formulations disclosed herein are packaged into discrete dosages each containing predetermined quantities of active compounds calculated based on the needs and medical history of the subject.

A "pharmaceutically-acceptable compound" is used to refer to a neutral complex. In some aspects, a pharmaceutically-acceptable compound may be more economical to produce, may have increased chemical stability, may allow manipulation of the compound's pharmacokinetics and bioavailability, may make the compound easier to administer, or a combination thereof. In a further aspect, a pharmaceutically-acceptable compound can alter a compound's dissolution or solubility. In one aspect, the pharmaceutically-acceptable compound can be an ionic compound. For example, the pharmaceutically-acceptable compound can be the reaction product between an organic acid (e.g., citric acid) and base (e.g., calcium hydroxide) to produce the ionic compound calcium citrate.

Throughout this specification, unless the context dictates otherwise, the word "comprise," or variations such as "comprises" or "comprising," will be understood to imply the inclusion of a stated integer or step or group of integers or steps but not the inclusion of any other integer or step or group of integers or steps.

References in the specification and concluding claims to parts by weight, of a particular element or component in a composition or article, denote the weight relationship between the element or component and any other elements or components in the composition or article for which a part by weight is expressed. Thus, in a compound containing 2 parts by weight of component X and 5 parts by weight of component Y, X and Y are present at a weight ratio of 2:5, and are present in such ratio regardless of whether additional components are contained in the compound.

As used herein, a plurality of items, structural elements, compositional elements, and/or materials may be presented in a common list for convenience. However, these lists should be construed as though each member of the list is individually identified as a separate and unique member. Thus, no individual member of any such list should be construed as a de facto equivalent of any other member of the same list based solely on its presentation in a common group, without indications to the contrary.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range was explicitly recited. As an illustration, a numerical range of "about 1 to about 5" should be interpreted to include not only the explicitly recited values of about 1 to about 5, but also to include individual values and sub-ranges within the indicated range. Thus, included in this numerical range are individual values such as 2, 3, and 4, the sub ranges such as from 1-3, from 2-4, from 3-5, etc., as well as 1, 2, 3, 4, and 5 individually. The same principle applies to ranges reciting only one numerical value as a minimum or maximum. Furthermore, such an interpretation should apply regardless of the breadth of the range or the characteristics being described.

Disclosed are materials and components that can be used for, can be used in conjunction with, can be used in preparation for, or are products of the disclosed compositions and methods. These and other materials are disclosed herein, and it is understood that when combinations, subsets, interactions, groups, etc., of these materials are disclosed, that while specific reference to each individual and collective combination and permutation of these compounds may not be explicitly disclosed, each is specifically contemplated and described herein. For example, if a water soluble vitamin is disclosed and discussed and a number of different minerals are discussed, each and every combination of water soluble vitamin and mineral that is possible is specifically contemplated unless specifically indicated to the contrary. For example, if a class of water soluble vitamins A, B, and C are disclosed, as well as a class of minerals D, E, and F, and an example combination of A+D is disclosed, then even if each is not individually recited, each is individually and collectively contemplated. Thus, in this example, each of the combinations A+E, A+F, B+D, B+E, B+F, C+D, C+E, and C+F is specifically contemplated and should be considered from disclosure of A, B, and C; D, E, and F; and the example combination of A+D. Likewise, any subset or combination of these is also specifically contemplated and disclosed. Thus, for example, the sub-group of A+E, B+F, and C+E is specifically contemplated and should be considered from disclosure of A, B, and C; D, E, and F; and the example combination of A+D. This concept applies to all aspects of the disclosure including, but not limited to, steps in methods of making and using the disclosed compositions. Thus, if there are a variety of additional steps that can be performed with any specific embodiment or combination of embodiments of the disclosed methods, each such combination is specifically contemplated and should be considered disclosed.

As used herein, a vitamin is an organic compound that is required in small quantities to support essential body functions including growth and cellular maintenance. In some aspects, vitamins cannot be produced by the body (e.g., vitamin C) or are not produced in sufficient quantities to meet a patient's needs and must be supplied via external sources. Handbook of Nonprescription Drugs, 11$^{th}$ edition, 1996, American Pharmaceutical Association. 2215 Constitution Avenue, NW, Washington, D.C. 20037. Chapter 19, Nutritional Products, page 361. In one aspect, many diets are insufficient in one or more key vitamins and supplements are often indicated, especially in the cases of chronically ill individuals such as patients undergoing kidney dialysis. In one aspect, a vitamin can act as a cofactor to assist an enzyme in carrying out an essential biochemical reaction.

In one aspect, the formulations disclosed herein include one or more water soluble vitamins. In one aspect, water-soluble vitamins are depleted during kidney dialysis and should be replenished to maintain overall health and well-being. In a further aspect, the supplement disclosed herein provides water-soluble vitamins including the B complex vitamins and vitamin C.

B Complex Vitamins

In one aspect, the formulations disclosed herein include one or more B vitamins. In this aspect, B vitamins generally act as cofactors or coenzymes or precursors needed to make cofactors or coenzymes. In a further aspect, B vitamins are not stored in the body and must be regularly supplied by dietary or other means to avoid deficiency. In one aspect, co-supplementation of vitamins $B_6$, $B_9$, and $B_{12}$ along with iron is especially effective against osteoporosis and anemia while also improving immune function. In a further aspect, all B complex vitamins can be used instead of just one or two.

In another aspect, low levels of B vitamins can affect the manufacture of neurotransmitters and contribute to stress and anxiety. In this aspect, supplementation of B vitamins can reduce stress related to their deficiency. In one aspect, low levels of B vitamins are caused by chronic kidney dialysis, the use of diuretics, and overconsumption of refined carbohydrates, since digestion of many carbohydrates requires the use of B vitamins. In one aspect, inadequate B vitamin intake is linked to blood sugar surges in patients who consume too many refined carbohydrates.

In one aspect, thiamin, or vitamin $B_1$, is included in the formulations disclosed herein. In this aspect, thiamin may be important to nerve and muscle health, production of hydrochloric acid in the stomach, and treatment of constipation and fatigue, as well as assisting digestion of some carbohydrates and proteins. In one aspect, the thiamine source is thiamine mononitrate. In one aspect, the amount of vitamin $B_1$ present per unit dose is from 0.1 mg to 50 mg, 0.1 mg to 25 mg, 0.1 mg to 10 mg, 0.1 mg to 5 mg, 0.1 mg to 2 mg, or 0.1 mg to 1 mg. In another aspect, 0.5 mg to 2 mg of thiamine is present per unit dose of the supplement.

In another aspect, riboflavin, or vitamin $B_2$, is included in the formulations disclosed herein. In this aspect, riboflavin may be important for growth, red blood cell production, and eye health, as well as assisting in the digestion of some carbohydrates, fats, ketone bodies, and proteins. In one aspect, the riboflavin source is molecular riboflavin. In one aspect, the amount of vitamin $B_2$ present per unit dose is from 0.1 mg to 2 mg, 0.5 mg to 2 mg, or 0.5 mg to 1 mg. In another aspect, 0.5 to 2 mg of riboflavin is present per unit dose of the supplement.

In still another aspect, nicotinic acid or nicotinamide, also known as niacinamide or vitamin $B_3$, is included in the formulations disclosed herein. Further in this aspect, vitamin $B_3$ is important to digestive system health and may assist in the digestion of some carbohydrates, as well as in the production of various sex and stress-related hormones. Still further in this aspect, niacin may be useful in reducing cholesterol levels in the blood. In one aspect, the niacinamide source is molecular niacinamide. In one aspect, the amount of vitamin $B_3$ present per unit dose is from 1 mg to 40 mg, 5 mg to 30 mg, or 5 mg to 25 mg. In another aspect, 5 to 25 mg of niacinamide is present per unit dose of the supplement.

In one aspect, the formulations disclosed herein include pantothenic acid, or vitamin $B_5$. In this aspect, pantothenic acid may be important for red blood cells production, digestive system health, adrenal gland health, and the digestion of some carbohydrates. In one aspect, the pantothenate source is D-calcium pantothenate. In one aspect, the amount of vitamin $B_5$ present per unit dose is from 1 mg to 20 mg, 1 mg to 15 mg, or 5 mg to 10 mg. In another aspect, 5 to 10 mg of L- or D-calcium pantothenate is present per unit dose of the supplement.

In another aspect, the formulations disclosed herein include pyridoxal phosphate (also occurring as pyridoxine), or vitamin $B_6$. Further in this aspect, pyridoxal phosphate may be important for brain health and the production of red blood cells and immune system cells. In a further aspect, deficiencies in vitamin $B_6$ have been linked to diabetes, nervous system disorders, and heart disease. In one aspect, the pyridoxine source is pyridoxine hydrochloride. In one aspect, the amount of vitamin $B_6$ present per unit dose is from 1 mg to 100 mg, 1 mg to 50 mg, or 1 mg to 10 mg. In another aspect, 1 to 10 mg of pyridoxine hydrochloride is present per unit dose of the supplement.

In still another aspect, the formulations disclosed herein include biotin, or vitamin $B_7$. In a further aspect, biotin is important to various aspects of metabolism and may be important in strengthening the hair and nails as well as in the metabolism of fats and amino acids. In one aspect, the biotin source is molecular biotin. In one aspect, the amount of vitamin $B_7$ present per unit dose is from 10 μg to 500 μg, 10 μg to 300 μg, or 10 μg to 100 μg. In another aspect, 10 to 100 μg of biotin is present per unit dose of the supplement.

In one aspect, the formulations disclosed herein include folate, also known as folic acid or vitamin $B_9$. Further in this aspect, folic acid may be important for brain function, mental health, red blood cells production, and production of nucleic acids. In one aspect, the folate source is folic acid. In one aspect, the amount of vitamin $B_9$ present per unit dose is from 0.05 mg to 1 mg, 0.1 mg to 1 mg, or 0.1 mg to 0.5 mg. In another aspect, 0.2 to 0.4 mg of folic acid is present per unit dose of the supplement.

In another aspect, cobalamin, or vitamin $B_{12}$, is included in the formulations disclosed herein. Further in this aspect, the cobalamin may be present as the cyanocobalamin, hydroxycobalamin, adenosylcobalamin, or methylcobalamin form. In another aspect, cobalamin is important to nervous system health, the production of red blood cells, and synthesis of nucleic acids. In a further aspect, cobalamin works synergistically with folate with respect to red blood cell production. In one aspect, the cobalamin source is cyanocobalamin. In one aspect, the amount of vitamin $B_{12}$ present per unit dose is from 1 μg to 150 μg, 1 μg to 100 μg, 1 μg to 50 μg, 1 μg to 25 μg, or 1 μg to 10 μg. In another aspect, 3 to 6 μg of cyanocobalamin is present per unit dose of the supplement.

Vitamin C

In one aspect, the formulations disclosed herein include ascorbic acid or vitamin C. In a further aspect, vitamin C is important to the immune system, collagen production, and wound healing. Further in this aspect, vitamin C is needed for the biosynthesis of hydroxyproline, which is important in the synthesis of collagen, osteoid, and dentin.

In a further aspect, vitamin C is a potent antioxidant that can fight free radical damage. In a still further aspect, vitamin C may assist with the uptake of non-heme iron. In yet another aspect, vitamin C helps to protect folate from oxidative damage.

In one aspect, the amount of vitamin C present per unit dose is from 10 mg to 2,000 mg, 10 mg to 1,500 mg, 10 mg to 1,000 mg, 100 mg to 500 mg, or 100 mg to 300 mg. In another aspect, 100 to 300 mg of vitamin C (as ascorbic acid) is provided per unit dose of the supplement.

Fat-soluble vitamins are absorbed in the small intestine and are stored in and can accumulate in body tissues. In some aspects, when excessive quantities of fat-soluble items are ingested, this can be toxic to the body.

Vitamins A, E, and K

In one aspect, vitamins A, E, and K can accumulate to toxic levels in body tissue of patients undergoing dialysis. Handbook of Nonprescription Drugs, 11$^{th}$ edition, 1996, American Pharmaceutical Association. 2215 Constitution Avenue, NW, Washington, D.C. 20037. Chapter 19, Nutritional Products, page 366. Further in this aspect, supplementation of these vitamins for kidney dialysis patients is contraindicated. In another aspect, the supplements disclosed herein do not include vitamins A, E, and K.

Vitamin D

In another aspect, vitamin D is a fat-soluble vitamin that is usually activated by healthy or well-functioning kidneys. In one aspect, in the case of kidney failure, the body cannot produce enough vitamin D and it should be supplemented in patients with kidney failure. However, in another aspect, a patient's medical providers may decide vitamin D supplementation is not required and/or would cause further harm. In any of the above aspects, the supplement may or may not include a source of vitamin D, to be given at the discretion of healthcare providers on a case-by-case basis.

In one aspect, when vitamin D is included in the formulations disclosed herein, it may improve bone health and immune system function and may protect against certain cancers. In a further aspect, vitamin D can increase calcium and phosphate absorption from the small intestine, is important in bone mineralization, and maintains proper calcium and phosphorus levels in the serum. Handbook of Nonprescription Drugs, 11$^{th}$ edition, 1996, American Pharmaceutical Association. 2215 Constitution Avenue, NW, Washington, D.C. 20037. Chapter 19, Nutritional Products, page 368.

In one aspect, the amount of vitamin D present per unit dose is from 1 μg to 100 μg, 1 μg to 50 μg, or 1 μg to 20 μg. In another aspect, 5 to 10 μg of vitamin D (as cholecalciferol) are provided per unit dose of the supplements disclosed herein.

As used herein, a mineral is an inorganic element that is obtained from food or supplementation and is required for the functioning of the human body. Minerals include, but are not limited to, calcium, chromium, copper, iron, magnesium, manganese, molybdenum, nickel, potassium, selenium, sodium, vanadium, cobalt, and zinc. In one aspect, a mineral can act as a cofactor. In other aspects, minerals can be used for cell signaling, or can be an essential structural component of the body (e.g., calcium in bone), or can associate with proteins, nucleic acids, lipids, and carbohydrates to maintain particular secondary, tertiary, and quaternary structures.

In another aspect, the mineral can be part of a chelate complex. Chelates have a cyclic structure in which a central metallic ion is held tight via covalent-coordinate bonds to form a coordinate compound, or, a chelate complex. Furthermore, chelates occur abundantly in nature; for example, chlorophyll complexed with magnesium, hemoglobin with iron, Vitamin B12 with cobalt hemocyanin with copper as well as enzymes that contain vanadium or molybdenum.

Chronic kidney dialysis can deplete the body of essential minerals. In this aspect, the supplements disclosed herein include a number of important minerals.

Calcium

In one aspect, the formulations disclosed herein include a pharmaceutically-acceptable compound of calcium. In a further aspect, calcium supplementation can be useful in preventing osteoporosis since calcium is a major component of bones and teeth. In a still further aspect, calcium's absorption and effects are enhanced or aided by vitamin D and parathyroid hormone. In still another aspect, calcium may be important to B complex vitamin absorption and is important to the functional integrity of many cells. In yet another aspect, calcium requirements may increase with increased protein consumption.

In one aspect, the calcium is provided as an ionic compound of calcium. Examples of such compounds include, but are not limited to, calcium citrate, calcium citrate tetrahydrate, calcium lactate pentahydrate, and calcium ascorbate. In one aspect, the formulations described herein include an ionic compound of calcium in an amount such that there is 100 mg to 2,500 mg, 100 mg to 2,000 mg, 100 mg to 1,500 mg, 100 mg to 1,000 mg, or 100 mg to 750 mg of calcium per unit dose. For example, calcium citrate tetrahydrate has a molecular weight of 570.49, of which calcium is 21.08%. Thus, in order for the formulation to have 500 mg of calcium per unit dose, there will be approximately 2,372.3 mg of calcium citrate tetrahydrate per unit dose. In another aspect, 250 to 500 mg of calcium is provided per unit dose of the supplements disclosed herein.

Magnesium

In one aspect, the formulations disclosed herein include a pharmaceutically-acceptable compound of magnesium. In a further aspect, magnesium is necessary for the proper functioning of calcium in the body such as, for example, assisting in entry of calcium ions into cells, thus preventing calcification of tissues. In some aspects, magnesium supplementation may support healthy heart function.

In one aspect, magnesium is required for normal bone structure formation and the functioning of several hundred enzymes, especially those with ATP-dependent phosphorylation, protein synthesis, and carbohydrate metabolism. In a further aspect, magnesium in the extracellular matrix is important to electrical potentials in nerve and muscle cells and the transmission of impulses across neuromuscular junctions.

In one aspect, the magnesium is provided as an ionic compound of magnesium. Examples of such compounds include, but are not limited to, magnesium citrate, magnesium sulfate monohydrate or heptahydrate, magnesium acetate tetrahydrate, magnesium D-gluconate hydrate, or magnesium nitrate hexahydrate. In one aspect, the formulations described herein include an ionic compound of magnesium in an amount such that there is 100 mg to 500 mg, 150 mg to 500 mg, 200 mg to 500 mg, 250 mg to 500 mg, or 300 mg to 500 mg of magnesium per unit dose.

Zinc

In one aspect, the formulations disclosed herein include a pharmaceutically-acceptable compound of zinc. In a further aspect, zinc is especially depleted (from 40% to 78%) during dialysis. In some aspects, zinc is anti-inflammatory, anti-depressant, and functions to support the immune system. Handbook of Nonprescription Drugs, 11$^{th}$ edition, 1996, American Pharmaceutical Association. 2215 Constitution Avenue, NW, Washington, D.C. 20037. Chapter 19, Nutritional Products, page 388.

In another aspect, zinc is integral to the function of many metalloenzymes and is a cofactor in the synthesis of nucleic acids. In a further aspect, zinc is important in the mobilization of vitamin A from the liver and in several reproductive system hormones and functions in both men and women.

In one aspect, the zinc is provided as an ionic compound of zinc. Examples of such compounds include, but are not limited to, zinc citrate, zinc citrate dihydrate, zinc acetate dihydrate, or zinc nitrate hexahydrate. In one aspect, the formulations described herein include an ionic compound of zinc in an amount such that there is 1 mg to 40 mg, 1 mg to 30 mg, 1 mg to 20 mg, or 5 mg to 20 mg of zinc per unit dose.

Selenium

In one aspect, the formulations disclosed herein include a pharmaceutically-acceptable compound of selenium. In a further aspect, selenium is highly concentrated in the liver and kidneys and is thus especially depleted during dialysis. In a still further aspect, selenium is a powerful antioxidant and is especially useful when employed against the damaging effects of free radicals. In another aspect, selenium supplementation may protect against hardening of the arteries and harmful molecules. Handbook of Nonprescription Drugs, 11$^{th}$ edition, 1996, American Pharmaceutical Association. 2215 Constitution Avenue, NW, Washington, D.C. 20037. Chapter 19, Nutritional Products, page 387.

In one aspect, the selenium is provided as an ionic compound of selenium such as, for example, sodium selenate. In one aspect, the formulations described herein include an ionic compound of selenium in an amount such that there is 10 μg to 400 μg, 10 μg to 300 μg, 10 μg to 200 μg, 10 μg to 100 μg, or 25 μg to 80 μg of selenium per unit dose.

Iron

In one aspect, the formulations disclosed herein include a pharmaceutically-acceptable compound of iron. In a further aspect, iron is vital in preventing anemia. Handbook of Nonprescription Drugs, 11$^{th}$ edition, 1996, American Pharmaceutical Association. 2215 Constitution Avenue, NW, Washington, D.C. 20037. Chapter 19, Nutritional Products, page 380. In still another aspect, biochemically, iron is important to oxygen and electron transport as well as prevent anemia and improve the quality and quantity of red blood cells. In a further aspect, heme iron is found in meats and is well-absorbed, while non-heme iron is poorly absorbed. In a still further aspect, supplementation of iron may be particularly important for patients consuming diets that include little or no meat.

In one aspect, the iron is provided as an ionic compound of iron such as, for example, iron gluconate, iron gluconate dihydrate, or iron sulfate heptahydrate. In one aspect, the formulations described herein include an ionic compound of iron in an amount such that there is 1 mg to 45 mg, 1 mg to 30 mg, 1 mg to 20 mg, or 5 mg to 20 mg of iron per unit dose.

In one aspect, the formulations disclosed herein incorporate one or more amino acids. In a further aspect, these amino acids can be proteinogenic or non-proteinogenic.

L-Carnitine

L-carnitine is a vitamin-like molecule that is used by the body to transport fatty acids into the mitochondria for breakdown. It is a non-proteinogenic amino acid that is synthesized in the liver and kidneys from lysine and methionine. This essential amino acid is completely or almost completely depleted from the blood with chronic kidney dialysis. L-carnitine deficiency has been linked to adverse cardiac conditions including, but not limited to, arrhythmias and angina; thus, in one aspect, supplementing with L-carnitine can reduce the incidence of cardiac damage and cardiac events associated with kidney dialysis. In a further aspect, L-carnitine deficiency has been shown to limit mitochondrial fat metabolism in the heart and other organs; in this aspect, supplementation with L-carnitine may help restore normal mitochondrial fat metabolism. In still another aspect, L-carnitine supplementation can provide support in cases of muscle weakness and may protect against circulatory disorders. In a still further aspect, L-carnitine has been shown to be important in oxidation of fatty acids and cellular energy management.

In one aspect, the formulations disclosed herein include pharmaceutically-acceptable compound of L-carnitine. Examples of pharmaceutically-acceptable compounds of L-carnitine include, but are not limited to, acetyl-L-carnitine or L-carnitine-L-tartrate, which can be metabolized in the blood by plasma esterases to produce L-carnitine. In other aspects, L-carnitine can be used directly. In one aspect, the amount of the pharmaceutically-acceptable compound of L-carnitine present per unit dose is from 100 mg to 3,500 mg, 500 mg to 2,500 mg, 500 mg to 1,000 mg, 1,000 mg to 2,000 mg of L-carnitine per unit dose. For example, 2,239 mg of L-carnitine-L-tartrate will provide 1,500 mg of L-carnitine per unit dose. In a further aspect, 500 mg to 2,500 mg of acetyl-L-carnitine or L-carnitine-L-tartrate is included in the supplements disclosed herein.

In one aspect, depending on the patient needs as assessed by the healthcare provider, additional ingredients can be included in the supplements disclosed herein.

Citrus Bioflavonoids

In one aspect, the formulations disclosed herein include citrus bioflavonoids. In a further aspect, citrus fruits are excellent sources of vitamin C and citrus bioflavonoid preparations sourced from whole citrus fruits or citrus rinds/peels or pith may be rich in vitamin C. In a further aspect, the citrus bioflavonoids can be from lemons, limes, grapefruits, oranges, tangerines, or a combination thereof. In a further aspect, the citrus bioflavonoids can include rutin, quercetin, tangeritin, diosmetin, diosmin, naringin, nairrutin, neohesperidin, nobiletin, hesperidin, and combinations thereof.

In a still further aspect, citrus bioflavonoids may be anti-inflammatory, antioxidant, or anti-microbial. In still another aspect, citrus bioflavonoids may improve capillary permeability and circulation, hypertension, swelling or edema, and insulin response, or a combination thereof. In still another aspect, sources of citrus bioflavonoids may contain flavor compounds that render the compositions disclosed herein more palatable.

Powdered Extract of Cranberry and Cherry

In one aspect, the formulations disclosed herein include powdered extracts of cranberry and cherry. In another aspect, cranberry and cherry extracts may contain flavor compounds that render the compositions disclosed herein more palatable. In a further aspect, cranberry and cherry extracts are high in antioxidants, vitamins, and minerals.

In a still further aspect, cranberry extract contains D-mannose, a sugar that has anti-biofilm (bacterial biofilm that is) properties, binds to and agglomerates bacteria in the urinary tract, thus helping to prevent urinary tract infections, which can be especially important for dialysis patients.

In one aspect, the cherry extract is from tart cherry. Further in this aspect, consumption of tart cherry extract may reduce side effects of statins, may improve blood cholesterol levels, may reduce inflammation related to arthritis and/or obesity, and may support a healthy metabolism.

In one aspect, some minerals are not to be included in the supplements disclosed herein.

Potassium

In one aspect, potassium is excluded from the formulations described herein. In some aspects, high potassium levels can cause muscle and heart problems. In a further aspect, potassium levels can rise between dialysis sessions and may affect the heartbeat.

Sodium

In another aspect, the formulations disclosed herein exclude sodium. In one aspect, increased sodium consumption causes thirst and may lead to water retention. In a further aspect, excess sodium consumption and/or high sodium levels can raise the blood pressure.

Phosphorus

In one aspect, the formulations disclosed herein exclude phosphorus. In a further aspect, too much phosphorus in the blood can cause calcium resorption from the bones. In still another aspect, too much phosphorus can cause the skin to itch. Handbook of Nonprescription Drugs, 11$^{th}$ edition, 1996, American Pharmaceutical Association. 2215 Constitution Avenue, NW, Washington, D.C. 20037. Chapter 19, Nutritional Products, page 383-384. In one aspect, a phosphate binder is provided to the patient alongside the formulations disclosed herein.

The supplements described herein can be formulated using techniques known in the art. In one aspect, the minerals, vitamins, and amino acids supplied in dry form are admixed with one another to produce a dry powder. In addition to the minerals, vitamins, and amino acids, other pharmaceutically-acceptable fillers can be added to formulate the supplement in powder form. For example, polysaccharides such as, for example, maltodextrin, can be used to formulate the supplement.

In one aspect, the supplement is a unit dose composition composed of
(a) vitamin B1
(b) vitamin B2
(c) vitamin B3
(d) vitamin B5
(e) vitamin B6
(f) vitamin B7
(g) vitamin B9
(h) vitamin B12
(i) vitamin C
(j) vitamin D$_3$
(k) a pharmaceutically-acceptable compound of calcium
(l) a pharmaceutically-acceptable compound of magnesium
(m) a pharmaceutically-acceptable compound of zinc
(n) a pharmaceutically-acceptable compound of selenium
(o) a pharmaceutically-acceptable compound of iron
(p) a pharmaceutically-acceptable compound of L-carnitine.

In another aspect, the supplement includes the following components in a dry powder:
(a) vitamin B1 in the amount of 0.1 mg to 50 mg per unit dose;
(b) vitamin B2 in the amount of 0.1 mg to 2 mg per unit dose;
(c) vitamin B3 in the amount of 1 mg to 40 mg per unit dose;
(d) vitamin B5 in the amount of 1 mg to 20 mg per unit dose;
(e) vitamin B6 in the amount of 1 mg to 100 mg per unit dose;
(f) vitamin B7 in the amount of 10 µg to 500 µg per unit dose;
(g) vitamin B9 in the amount of 0.05 mg to 1.0 mg per unit dose;
(h) vitamin B12 in the amount of 1 µg to 150 µg per unit dose;
(i) vitamin C in the amount of 10 mg to 2,000 mg per unit dose;
(j) vitamin D$_3$ in the amount of 1 µg to 100 µg per unit dose;
(k) a pharmaceutically-acceptable compound of calcium in the amount of 100 mg to 2,500 mg per unit dose;
(l) a pharmaceutically-acceptable compound of magnesium in the amount of 100 mg to 500 mg per unit dose;
(m) a pharmaceutically-acceptable compound of zinc in the amount of 1 mg to 40 mg per unit dose;
(n) a pharmaceutically-acceptable compound of selenium in the amount of 10 µg to 400 µg per unit dose;
(o) a pharmaceutically-acceptable compound of iron in the amount of 1 mg to 45 mg per unit dose; and
(p) a pharmaceutically-acceptable compound of L-carnitine in the amount of 100 mg to 3,500 mg per unit dose.

In another aspect, the supplement includes the following components in a dry powder:
(a) vitamin B1 in the amount of 0.5 mg to 2 mg per unit dose;
(b) vitamin B2 in the amount of 0.5 mg to 2 mg per unit dose;
(c) vitamin B3 in the amount of 1 mg to 20 mg per unit dose;
(d) vitamin B5 in the amount of 1 mg to 15 mg per unit dose;
(e) vitamin B6 in the amount of 1 mg to 10 mg per unit dose;
(f) vitamin B7 in the amount of 10 g to 100 µg per unit dose;
(g) vitamin B9 in the amount of 0.1 mg to 1.0 mg per unit dose;
(h) vitamin B12 in the amount of 1 µg to 10 µg per unit dose;
(i) vitamin C in the amount of 100 mg to 300 mg per unit dose;
(j) vitamin D$_3$ in the amount of 1 µg to 20 µg per unit dose;
(k) a pharmaceutically-acceptable compound of calcium in the amount of 100 mg to 1,000 mg per unit dose;
(l) a pharmaceutically-acceptable compound of magnesium in the amount of 100 mg to 500 mg per unit dose;
(m) a pharmaceutically-acceptable compound of zinc in the amount of 5 mg to 20 mg per unit dose;
(n) a pharmaceutically-acceptable compound of selenium in the amount of 10 µg to 100 µg per unit dose;
(o) a pharmaceutically-acceptable compound of iron in the amount of 5 mg to 30 mg per unit dose; and
(p) L-carnitine-L-tartrate in the amount of 1,000 mg to 3,000 mg per unit dose.

In another aspect, the supplement has the following components as provided in Table 1.

TABLE 1

Formulation of a Representative Nutritional Supplement

| Component | Amount Per Unit Dose | Source |
| --- | --- | --- |
| Vitamin B$_1$ | 1.5 mg | Thiamine Mononitrate |
| Vitamin B$_2$ | 1.7 mg | Riboflavin |
| Vitamin B$_3$ | 20 mg | Niacinamide |
| Vitamin B$_5$ | 10 mg | D-Calcium Pantothenate |
| Vitamin B$_6$ | 15 mg | Pyridoxine Hydrochloride |
| Vitamin B$_7$ | 100 µg | Biotin |
| Vitamin B$_9$ | 1 mg | Folic Acid |
| Vitamin B$_{12}$ | 6 µg | Cyanocobalamin |
| Vitamin C | 250 mg | Ascorbic Acid |
| Vitamin D$_3$ | 10 µg | Cholecalciferol |
| Calcium | 500 mg | Calcium Citrate |
| Magnesium | 400 mg | Magnesium Citrate |
| Zinc | 15 mg | Zinc Citrate |
| Selenium | 70 µg | Sodium Selenate |
| Iron | 18 mg | Iron Gluconate |

TABLE 1-continued

Formulation of a Representative Nutritional Supplement

| Component | Amount Per Unit Dose | Source |
| --- | --- | --- |
| Marine Omega 3 Fatty Acids | 1000 mg | Wild Alaskan Salmon Oil or Marine Algal Oil, EPA:DHA ratio is from 1:1 to 4:1. |
| L-Carnitine | 1500 mg | Acetyl-L-Carnitine or L-Carnitine-L-Tartrate |
| Coenzyme Q10H2 | 200 mg | Ubiquinol |
| Turmeric | 2 g (optional) | Ground Spice or Extract |
| Citrus Bioflavonoids | (optional) | Ground Rind or Extract |
| Extract of Cranberry and Cherry Powders | (optional) | Extract of Dried, Powdered Fruits |

The supplements described herein are intended to be taken orally. In one aspect, the supplements can be formulated as tablets or capsules. In other aspects, the supplements can be formulated as a powder that can be mixed with water or another beverage. Alternatively, the powder form of the supplement can be admixed with food such as yogurt, peanut butter, or other foods that readily mix with the supplement.

The formulations described herein are to be administered to patients with kidney disease and/or undergoing kidney dialysis, or individuals at risk of kidney diseases (lifestyle, family history, etc.). The amount of formulation administered to the patient should not exceed the recommended daily dose for each component. The formulations can be administered to the patient prior to dialysis, during dialysis, after dialysis, and any combination thereof. The nutritional supplement described herein is designed to support kidney and cardiac function as well as mitochondrial energy function needs in patients undergoing hemodialysis. This supplement replenishes essential vitamins and minerals that are lost during dialysis, does not contain compounds that may specifically cause harm to dialysis patients, and provides support for tissues undergoing oxidative stress. By replenishing the minerals and vitamins lost during dialysis, the subject will have increased energy levels that will permit the subject to lead a more productive life.

One or more additional supplements can be taken with the supplements described herein. In one aspect, an omega 3 fatty acid can be taken with the supplements described herein. Omega 3 fatty acids are lipid soluble macronutrients that are important to metabolism (i.e., energy production captured in the form of ATP). Omega 3 fatty acids are partially removed from the body with chronic kidney dialysis. Omega 3 fatty acids have been shown to reduce inflammation and thus to lower the risk of chronic diseases (including heart disease). They are believed to be important for cognitive function and also have been shown to reduce triglycerides while increasing high-density lipoproteins (HDL) cholesterol. Omega 3 fatty acids have been linked to improvement in a number of other conditions including from skin, joint, eye, and gastrointestinal conditions. In one aspect, supplementation with omega 3 fatty acids can be especially important for improving blood pressure, blood circulation, and blood vessel elasticity while preventing cardiovascular and coronary events in persons with high cardiovascular risk. Marine Omega 3 Fatty Acids (www.wikipedia.org)

Omega 3 fatty acids are found in fish, some plants, nut oils, and algae, and are not always consumed in high enough amounts through the standard diet. In one aspect, it is important to replenish the body's supply of omega 3 fatty acids, since these important macronutrients cannot be synthesized by the body. In another aspect, marine omega 3 fatty acids (i.e., from fish or algae) have preferable amounts of DHA (docosahexaenoic acid) and EPA (eicosapentaenoic acid) as compared to omega 3 fatty acids from plant sources, which primarily contain ALA (alpha linolenic acid), a compound that is not efficiently utilized by the body.

In still another aspect, the formulations disclosed herein include marine omega 3 fatty acids. In a further aspect, the marine omega 3 fatty acids can be sourced from salmon, mackerel, sardines, tuna, or herring. Many Western diets incorporate higher dietary omega 6 fatty acids, which can promote inflammation. In another aspect, it is important to supplement omega 3 fatty acids, especially in hemodialysis patients, to reduce inflammation and the risk of death. In another aspect, the amount of Omega 3 is significantly higher than the amount Omega 6.

In yet another aspect, hemodialysis is believed to upregulate oxidative mechanisms, which could lead to peroxidation of omega 3 fatty acids; this, in turn, can lead to breakdown of the fatty acid structure and loss of function. In this aspect, supplementation with omega 3 fatty acids can be used to replenish the supply of nutrients destroyed by peroxidation.

In one aspect, the marine omega 3 fatty acids are provided as wild Alaskan salmon oil or marine algal oil. In a further aspect, the EPA:DHA ratio of the marine omega 3 fatty acids is from 1:1 to 4:1. In one aspect, the amount of marine omega 3 fatty acids present per unit dose is from 500 mg to 4,000 mg, 500 mg to 3,000 mg, 500 mg to 2,000 mg, or 500 mg to 1,500 mg. In another aspect, 1000 mg of marine omega 3 fatty acids are provided per unit dose of the supplements disclosed herein.

In another aspect, coenzyme Q10 (CoQ10) can be taken with the supplements described herein. CoQ10 acts as an antioxidant and protects the cell membrane against oxidative stress. In another aspect, CoQ10 is an important coenzyme in the mitochondria (and other parts of the cell) and participates in cellular respiration, which ultimately generates energy in the form of adenosine triphosphate. In still another aspect, CoQ10 protects against low-density lipoproteins (LDL) oxidation, which is vital for heart health. In a further aspect, reduced form of CoQ10 (CoQ10H$_2$) can regenerate vitamin E from the alpha-tocopheroxyl radical, thus leading to a reduction of oxidative stress.

In one aspect, certain patients require intake of CoQ10 that is higher than provided by the average diet. These include, but are not limited to, athletes, patients with hyperthyroidism, patients who are taking statins, and the elderly. Thus, in one aspect, elderly dialysis patients may especially benefit from CoQ10 supplementation. In a related aspect, CoQ10 can decrease insulin requirements in patients with diabetes; thus, diabetic dialysis patients may also benefit from CoQ10 supplementation.

In another aspect, however, CoQ10 supplementation should be avoided in patients taking warfarin or other blood thinners, as it can reduce the activity of these medications. In this aspect, the supplements disclosed herein do not include CoQ10.

In one aspect, CoQ10 in the supplements disclosed herein is provided as ubiquinol, a reduced form of CoQ10 that has a particularly high uptake percentage and subsequently leads to an increase of CoQ10 levels in the blood. Ubiquinol effectively regenerates vitamin E from alpha-tocopherol radical. In one aspect, the amount of CoQ10H$_2$ (e.g., ubiquinol) present per unit dose is from 70 mg to 400 mg, 70 mg to 300 mg, or 150 mg to 250 mg. In another aspect, 200 mg of ubiquinol are included in the supplements disclosed herein.

In one aspect, turmeric can be taken with the supplements described herein. Turmeric has anti-inflammatory and antioxidant properties that are in some aspects useful to the kidneys. In another aspect, the formulations disclosed herein do not include turmeric. In some aspects, turmeric should not be given to patients who are sensitive or allergic, pregnant or nursing, diabetic and taking blood thinners, patients with gall bladder conditions, and/or patients with digestive system disorders such as GERD (gastroesophageal reflux disease). In one aspect, turmeric is prepared in a separate distribution form (e.g., a separate capsule) and given to patients at their healthcare providers' discretion. In still another aspect, turmeric is provided with the supplement unless the patient is going to undergo surgery and/or has a bleeding disorder, since turmeric is known to be a powerful blood thinner.

In one aspect, pepperine can be taken with the supplements described herein. In some aspects, turmeric is not easily absorbed by the body and pepperine enhances absorption by 10 to 20 fold. In one aspect, the formulations disclosed herein include 100 mg of pepperine for every 500 mg of turmeric. In one aspect, the amount of turmeric present per unit dose is from 1 g to 3 g, 1.5 g to 2.5 g, or 2 g.

In one aspect, the supplements is formulated as a kit, where one compartment or vial has a mixture of the supplement described herein composed of the minerals, vitamins, and amino acids supplied in dry form (e.g., tablet, powder), and a second compartment of containing other supplements (e.g., marine omega 3 fatty acids in capsule form, ubiquinol in gel form, turmeric is in a capsule, or any combination thereof).

EXAMPLES

The following examples are put forth so as to provide those of ordinary skill in the art with a complete disclosure and description of how the materials, articles, and methods described and claimed herein are made and evaluated, and are intended to be purely exemplary and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

The components in Table 2 were admixed with one another in dry form to produce a supplement. Maltodextrin was added in an amount so that 8.5 g of supplement was produced.

TABLE 2

| Component | Amount Per Unit Dose | Source |
|---|---|---|
| Vitamin $B_1$ | 1.5 mg | Thiamine Mononitrate |
| Vitamin $B_2$ | 1.7 mg | Riboflavin |
| Vitamin $B_3$ | 20 mg | Niacin |
| Vitamin $B_5$ | 10 mg | D-Calcium Pantothenate |

TABLE 2-continued

| Component | Amount Per Unit Dose | Source |
|---|---|---|
| Vitamin $B_6$ | 5 mg | Pyridoxine Hydrochloride |
| Vitamin $B_7$ | 0.1 mg | Biotin |
| Vitamin $B_9$ | 0.4 mg | Folic Acid |
| Vitamin $B_{12}$ | 6 µg | Cyanocobalamin |
| Vitamin C | 250 mg | Ascorbic Acid |
| Vitamin $D_3$ | 10 µg | Cholecalciferol |
| Calcium | 500 mg | Calcium Citrate |
| Magnesium | 400 mg | Magnesium Citrate |
| Zinc | 15 mg | Zinc Citrate |
| Selenium | 70 µg | Sodium Selenate |
| Iron | 18 mg | Iron Gluconate |
| L-Carnitine | 1500 mg | L-Carnitine-L-Tartrate (2239 mg) |
| Citrus Bioflavonoids | 50 mg | |

A supplement described herein was evaluated with a subject undergoing dialysis. The subject has been treated for dialysis for the last 20 years and for the last 13 years at his home. Dialysis is conducted at home every other night for 7 hours.

The subject initially started taking a full dose of the supplements (8.5 g of the supplement provided in Table 2). However, the doze of the supplement was adjusted to a half dose. The subject took a quarter of the supplement together with fast carbohydrates for breakfast and the same dose for lunch with fast carbohydrates.

After three weeks, the subject's mental condition improved. The subject did not need to sleep so much as before. The subject has more energy and is able to do more activities such as play golf.

After taking the supplement for about six weeks, the subject has more energy and able to perform more outdoor activities (e.g., play 18 holes of golf). The subject perspires much more compared to when he was not taking the supplement, which is positive for dialysis patients that have problems getting rid of excess liquid in their body. The subject is also sleeping very well and is more focused. The subject's blood pressure is good. Renal blood samples are also good except for the level of sodium, which has been adjusted due to dialysis treatment.

Throughout this publication, various publications are referenced. The disclosures of these publications in their entireties are hereby incorporated by reference into this application in order to more fully describe the methods, compositions, and compounds herein.

Various modifications and variations can be made to the materials, methods, and articles described herein. Other aspects of the materials, methods, and articles described herein will be apparent from consideration of the specification and practice of the materials, methods, and articles disclosed herein. It is intended that the specification and examples be considered as exemplary.

What is claimed:

1. A kit for a subject (i) with kidney disease or at risk of kidney disease or (ii) undergoing kidney dialysis comprising the following components:
   (a) a unit dose composition consisting of;
      vitamin $B_1$ in the amount of 0.1 mg to 50 mg per unit dose;
      vitamin $B_2$ in the amount of 0.1 mg to 2 mg per unit dose;
      vitamin $B_3$ in the amount of 1 mg to 40 mg per unit dose;
      vitamin $B_5$ in the amount of 1 mg to 20 mg per unit dose;

vitamin $B_6$ in the amount of 1 mg to 100 mg per unit dose;
vitamin $B_7$ in the amount of 10 µg to 500 µg per unit dose;
vitamin $B_9$ in the amount of 0.05 mg to 1.0 mg per unit dose;
vitamin $B_{12}$ in the amount of 1 µg to 150 µg per unit dose;
vitamin C in the amount of 10 mg to 2,000 mg per unit dose;
a pharmaceutically-acceptable compound of calcium in the amount of 100 mg to 2,500 mg per unit dose;
vitamin $D_3$ in the amount of 1 µg to 100 µg per unit dose;
a pharmaceutically-acceptable compound of magnesium in the amount of 100 mg to 500 mg per unit dose;
a pharmaceutically-acceptable compound of zinc in the amount of 1 mg to 40 mg per unit dose;
a pharmaceutically-acceptable compound of selenium in the amount of 10 µg to 400 µg per unit dose;
a pharmaceutically-acceptable compound of iron in the amount of 1 mg to 45 mg per unit dose;
L-carnitine-L-tartrate or acetyl-L-carnitine;
maltodextrin; and
optionally a citrus bioflavonoid, powdered extract of cranberry or cherry, or any combination thereof;
(b) a capsule comprising marine omega 3 fatty acids in the amount of 500 mg to 4,000 mg per unit dose; and
(c) a gel comprising coenzyme Q10 in the amount of 70 mg to 400 mg per unit dose.

2. The kit of claim 1, wherein the marine omega 3 fatty acids comprise docosahexaenoic acid (DHA) and eicosapentaenoic acid (EPA) in the weight ratio (EPA:DHA) of 1:1 to 4:1.

3. The kit of claim 1, wherein coenzyme Q10 is ubiquinol.

4. The kit of claim 1, wherein the kit further comprises a capsule comprising turmeric, wherein the turmeric is in the amount of 1 g to 3 g per unit dose.

5. The kit of claim 1, wherein the calcium is calcium citrate, the magnesium is magnesium citrate, the zinc is zinc citrate; the selenium is sodium selenate; and the iron is iron gluconate.

6. The kit of claim 1, a citrus bioflavonoid, a powdered extract of cranberry and/or cherry, or a combination thereof is present in component (a).

7. The kit of claim 1, wherein component (a) consists of
vitamin $B_1$ in the amount of 0.5 mg to 2 mg per unit dose;
vitamin $B_2$ in the amount of 0.5 mg to 2 mg per unit dose;
vitamin $B_3$ in the amount of 1 mg to 20 mg per unit dose;
vitamin $B_5$ in the amount of 1 mg to 15 mg per unit dose;
vitamin $B_6$ in the amount of 1 mg to 10 mg per unit dose;
vitamin $B_7$ in the amount of 10 µg to 100 µg per unit dose;
vitamin $B_9$ in the amount of 0.1 mg to 1.0 mg per unit dose;
vitamin $B_{12}$ in the amount of 1 µg to 10 µg per unit dose;
vitamin C in the amount of 100 mg to 300 mg per unit dose;
a pharmaceutically-acceptable compound of calcium in the amount of 100 mg to 1,000 mg per unit dose;
vitamin $D_3$ in the amount of 1 µg to 100 µg per unit dose;
a pharmaceutically-acceptable compound of magnesium in the amount of 100 mg to 500 mg per unit dose;
a pharmaceutically-acceptable compound of zinc in the amount of 5 mg to 20 mg per unit dose;
a pharmaceutically-acceptable compound of selenium in the amount of 10 µg to 100 µg per unit dose;
a pharmaceutically-acceptable compound of iron in the amount of 5 mg to 30 mg per unit dose;
L-carnitine-L-tartrate or acetyl-L-carnitine;
maltodextrin; and
optionally a citrus bioflavonoid, powdered extract of cranberry or cherry, or any combination thereof.

8. The kit of claim 1, wherein the citrus bioflavonoid and powdered extract of cranberry or cherry are present in the composition.

9. A method for replenishing vitamins and minerals in a subject (i) having kidney disease or at risk of kidney disease or (ii) undergoing kidney dialysis comprising administering to the subject the components in the kit of claim 1.

10. The method of claim 9, wherein the method increases the energy level of the subject.

* * * * *